US012268364B2

(12) United States Patent
Krimsky et al.

(10) Patent No.: US 12,268,364 B2
(45) Date of Patent: *Apr. 8, 2025

(54) RAIL SYSTEM FOR USE WITH A BRONCHOSCOPE

(71) Applicant: Covidien LP, Mansfield, MA (US)

(72) Inventors: William S. Krimsky, Forest Hill, MD (US); William J. Dickhans, Longmont, CO (US); Joshua B. Stopek, Minneapolis, MN (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/484,540

(22) Filed: Oct. 11, 2023

(65) Prior Publication Data

US 2024/0049954 A1 Feb. 15, 2024

Related U.S. Application Data

(63) Continuation of application No. 17/083,404, filed on Oct. 29, 2020, now Pat. No. 11,793,395, which is a
(Continued)

(51) Int. Cl.
*A61B 1/018* (2006.01)
*A61B 1/00* (2006.01)
(Continued)

(52) U.S. Cl.
CPC .......... *A61B 1/018* (2013.01); *A61B 1/00128* (2013.01); *A61B 1/00133* (2013.01);
(Continued)

(58) Field of Classification Search
CPC ............ A61B 1/00128; A61B 1/00133; A61B 1/0125; A61B 1/015; A61B 1/018;
(Continued)

(56) References Cited

U.S. PATENT DOCUMENTS

| 3,830,225 A | 8/1974 | Shinnick |
| 6,419,654 B1 * | 7/2002 | Kadan .................. A61B 1/3132 600/101 |

(Continued)

FOREIGN PATENT DOCUMENTS

| JP | H0521901 U | 3/1993 |
| WO | 2010023460 A1 | 3/2010 |
| WO | 2013110073 A1 | 7/2013 |

OTHER PUBLICATIONS

Canadian Office Action dated May 3, 2019 issued in corresponding CA Appln. No. 3,015,982.
(Continued)

*Primary Examiner* — Aaron B Fairchild
(74) *Attorney, Agent, or Firm* — Weber Rosselli & Cannon LLP (57) ABSTRACT

A surgical system includes a bronchoscope, an extended working channel defining an elongated passageway and adapted to extend through the bronchoscope, and a valve in fluid communication with the passageway of the extended working channel. The surgical system further includes an elongated surgical instrument configured and dimensioned to be inserted through the extended working channel. During operation, a fluid is able to flow from the valve and through the extended working channel such that the fluid travels within an annular area surrounding the elongated surgical instrument positioned within the extended working channel.

8 Claims, 12 Drawing Sheets

Related U.S. Application Data continuation of application No. 15/435,485, filed on Feb. 17, 2017, now Pat. No. 10,856,729.

(60) Provisional application No. 62/301,224, filed on Feb. 29, 2016.

(51) Int. Cl.
*A61B 1/015* (2006.01)
*A61B 1/267* (2006.01)
*A61B 18/18* (2006.01)
*A61B 18/00* (2006.01)

(52) U.S. Cl.
CPC ............ *A61B 1/015* (2013.01); *A61B 1/2676* (2013.01); *A61B 18/1815* (2013.01); *A61B 2018/00029* (2013.01); *A61B 2018/00541* (2013.01); *A61B 2018/00577* (2013.01); *A61B 2018/1861* (2013.01)

(58) Field of Classification Search
CPC ............ A61B 1/2676; A61M 25/0028; A61M 39/022; A61M 39/225
See application file for complete search history.

(56) References Cited

U.S. PATENT DOCUMENTS

| | | |
|---|---|---|
| 8,795,155 B2 | 8/2014 | Kanazawa |
| 10,856,729 B2 | 12/2020 | Krimsky et al. |
| 11,793,395 B2 | 10/2023 | Krimsky et al. |
| 2003/0083545 A1 | 5/2003 | Smith |
| 2005/0027165 A1 | 2/2005 | Rovegno |
| 2006/0149127 A1* | 7/2006 | Seddiqui ............ A61B 1/0052 600/104 |
| 2009/0270677 A1* | 10/2009 | Dillon ............ A61B 90/50 600/106 |
| 2010/0240956 A1 | 9/2010 | Secrest et al. |
| 2010/0312141 A1 | 12/2010 | Keast |
| 2011/0264005 A1 | 10/2011 | Willeford et al. |
| 2014/0046174 A1 | 2/2014 | Ladtkow et al. |
| 2014/0276033 A1 | 9/2014 | Brannan et al. |
| 2015/0066005 A1 | 3/2015 | Fan et al. |
| 2015/0073211 A1 | 3/2015 | Dickhans et al. |

OTHER PUBLICATIONS

PCT Notification of Transmittal of the International Search Report and the Written Opinion for PCT/US2017/018620 dated Jun. 7, 2017.

Australian Office Action issued in Australian Application No. 2017225512 dated Nov. 30, 2018, 4 pages.

Extended European Search Report dated Sep. 13, 2019 issued in corresponding EP Appln. No. 17760483.2.

Australian Examination Report dated Jun. 28, 2019 issued in corresponding AU Appln. No. 2017225512.

Australian Examination Report dated Sep. 19, 2019 issued in corresponding AU Appln. No. 2017225512.

Final Office Action issued in corresponding Japanese Appl. No. 2018-545283 mailed Jan. 15, 2021 (3 pages), together with English language translation (4 pages).

Office Action issued in corresponding Japanese Application 2021-082228 dated May 19, 2022 (2 pages) (English translation not available).

* cited by examiner

RAIL SYSTEM FOR USE WITH A BRONCHOSCOPE

CROSS REFERENCE TO RELATED APPLICATIONS

This application is a continuation of U.S. patent application Ser. No. 17/083,404, filed on Oct. 29, 2020, now U.S. Pat. No. 11,793,395, which is a continuation of U.S. patent application Ser. No. 15/435,485, filed on Feb. 17, 2017, now U.S. Pat. No. 10,856,729, which claims the benefit of the filing date of provisional U.S. Patent Application No. 62/301,224, filed on Feb. 29, 2016.

FIELD

The present disclosure relates generally to treatment of patients with lung diseases, and, more particularly, to a navigation system and method for ablation catheters and other endobronchial tools.

BACKGROUND

A common interventional procedure in the field of pulmonary medicine is bronchoscopy, in which a bronchoscope is inserted into the airways through the patient's nose or mouth. The structure of a bronchoscope generally includes a long, thin, flexible tube that typically contains three elements: an illumination assembly for illuminating the region distal to the bronchoscope's tip via an optical fiber connected to an external light source; an imaging assembly for delivering back a video image from the bronchoscope's distal tip; and a lumen (or lumens) or working channel through which instruments or materials may be inserted, including but not limited to placement (e.g., guide wires), diagnostic (e.g., biopsy tools), therapeutic (e.g., treatment catheters or laser, cryogenic, radio frequency, or microwave tissue treatment probes) instruments and other materials such as medications, etc. The distal tip of a bronchoscope is steerable. Rotating a lever placed at the handle of the bronchoscope actuates a steering mechanism that deflects the tip in one or more directions.

Bronchoscopies are performed by pulmonologists, also known as bronchoscopists, and are used routinely in the diagnosis and treatment of conditions such as lung cancer, airway stenosis, and emphysema. Bronchoscopies are typically performed by a staff of at least two persons: the bronchoscopist and at least one assistant, usually a nurse. During a typical procedure, the bronchoscopist holds the bronchoscope handle with one hand and the bronchoscope tube with the other hand. The bronchoscopist manipulates the distal tip of the bronchoscope inside the lung by rotating a deflection lever and by pushing and pulling the tube. Once the tip is brought to a target, an instrument can be inserted into the working channel to perform a diagnostic or therapeutic procedure.

During insertion and operation of the instruments, the distal tip of the bronchoscope should be held steady at the target. Two hands are needed to secure the bronchoscope in place and one to two more hands are needed for inserting and actuating the instrument. Generally, the bronchoscopist releases the bronchoscope to insert and actuate the instrument. Performing a procedure that requires two people is generally more expensive and the potential for error is increased. Hence, it is desirable to modify a procedure so that it may be performed with one or two hands, if possible.

Additionally, because all of the instruments used with a bronchoscope are necessarily long and slender, the instruments do not retain shape when unsupported. Thus, inserting an instrument into a bronchoscope can be difficult or impossible to do quickly with one hand. While this problem can be addressed easily by holding the end of the sheath in one hand and the instrument in another, this would again require additional free hands during performance of the procedure.

During particular procedures (e.g., microwave ablation and biopsy) a catheter or extended working channel may be inserted through a working channel to enable navigation to different sites, typically more distal areas of the lungs. An instrument may be inserted through the catheter or extended working channel in order to perform a biopsy or ablation procedure. Current systems and methodologies for extending the surgical instrument from the catheter or retracting the catheter from the placement of the surgical instrument require at least two people to manipulate all the elements of the system including the bronchoscope.

Accordingly, there is a need for an apparatus that would facilitate one-handed actuation of the catheter and surgical instrument leaving one hand to manipulate the bronchoscope. In addition, there is a need for a support for use with a bronchoscope that would facilitate operation of a bronchoscope and associated tools by a single practitioner. It would also be advantageous to provide a support for the probe and the catheter to allow a single practitioner to manipulate a catheter, a probe, and a bronchoscope during the procedure.

SUMMARY

In one aspect, the present disclosure is directed to a surgical system. The surgical system includes a bronchoscope, an extended working channel defining an elongated passageway and adapted to extend through the bronchoscope, and a valve in fluid communication with the passageway of the extended working channel. The surgical system further includes an elongated surgical instrument configured and dimensioned to be inserted through the extended working channel. During operation, a fluid is able to flow from the valve and through the extended working channel such that the fluid travels within an annular area surrounding the elongated surgical instrument positioned within the extended working channel.

In disclosed embodiments, the valve is a one-way valve. Alternatively the valve is a three-way valve.

In disclosed embodiments, the fluid is at least one of the following: a pharmaceutical agent, a contrast agent, a sensitizing agent, a coagulation agent, a therapeutic agent, a diagnostic agent, a hemostasis agent, an antibiotic, and combinations of two or more of these.

In disclosed embodiments, the surgical system further includes a bronchoscope support system.

In one aspect, the present disclosure is directed to a surgical system. The surgical system includes a bronchoscope, an extended working channel adapted to extend through the bronchoscope, and a side port defining an elongated passageway and being in fluid communication with an opening formed through an exterior surface of the extended working channel. The surgical system further includes a valve in fluid communication with the side port, and an elongated surgical instrument configured and dimensioned to be inserted through the extended working channel.

In one aspect, the present disclosure is directed to a method of positioning an elongated surgical instrument adjacent targeted tissue. The method includes inserting the elongated surgical instrument into an extended working channel, the elongated surgical instrument having a locatable guide adjacent a distal end thereof, the extended working channel passing through a bronchoscope positioned in an airway of a patient, enabling fluid communication between a valve and the extended working channel, manipulating a portion of the extended working channel such that the elongated surgical instrument moves in concert with the portion of the extended working channel, and allowing fluid flow through the extended working channel.

In one aspect, the present disclosure is directed to a method of positioning an elongated surgical instrument adjacent targeted tissue. The method includes inserting the elongated surgical instrument into an extended working channel, the elongated surgical instrument having a locatable guide adjacent a distal end thereof, the extended working channel passing through a bronchoscope positioned in an airway of a patient, enabling fluid communication between the side port of the extended working channel, manipulating a portion of the extended working channel such that the elongated surgical instrument moves in concert with the portion of the extended working channel, and enabling fluid flow through the side port.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, which are incorporated in and constitute a part of this specification, wherein.

DETAILED DESCRIPTION

According to aspects of the present disclosure, a support system mounts to a bronchoscope to support instruments inserted through and associated with the bronchoscope. In one embodiment, the support system is configured to separately support a handle and a catheter inserted through the handle and the bronchoscope. The handle is coupled to an extended working channel that passes through the bronchoscope and into the anatomy of a patient. The catheter is inserted through the extended working channel to a position adjacent targeted tissue. The extended working channel is connected to a valve, such as a one-way valve or a three-way stop cock valve, for the delivery of different types of agents or fluids to a target site.

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" refers to the portion of the device or component thereof that is closest to the clinician and the term "distal" refers to the portion of the device or component thereof that is farthest from the clinician.

As it is used herein, the term "patient" generally refers to a human or other animal. For the purposes of this description, the term "fluid" generally refers to a gas, a liquid, or a mixture of gas and liquid. As it is used herein, the term "beneficial agent" generally refers to any physiologically active substance(s), pharmacologically active substance(s), and/or psychotropic substance(s).

Figure 1:
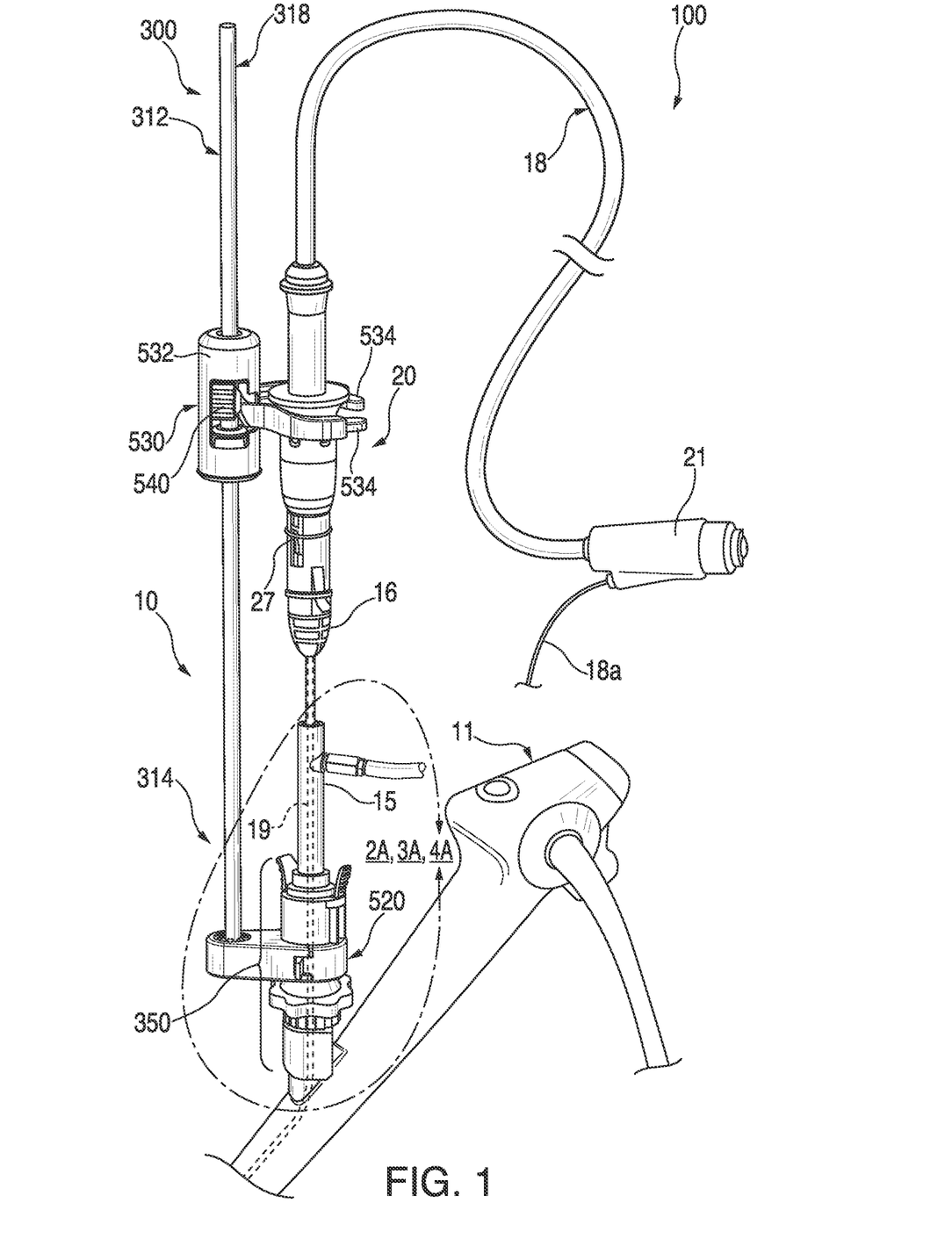
FIG. 1 illustrates a navigation system in accordance with aspects of the present disclosure.

Referring now to FIG. 1, a navigation system or surgical system 10 includes a bronchoscope 11, an extended working channel (EWC) 15, an ablation catheter assembly 100, including a cable 18, a probe 19, a handle 20, and a connector 21 for connection to an energy source such as a microwave generator (not shown). A portion 18a of the cable 18 may extend from the connector 21 to a coolant source (not shown) for providing a cooling fluid to the ablation catheter assembly 100. FIG. 1 also depicts a rail system 300 including a support rail 312 supported on the bronchoscope 11 by a lower support member 520 and includes a device support 530 that supports the handle 20.

The EWC 15 connects to the bronchoscope 11, such that instruments pass through the EWC 15. The proximal end 16 of the EWC 15 includes a mating feature that is engaged by the handle 20. For microwave ablation, the handle 20 mates with the proximal end 16 of the EWC 15, thus enabling movement of the EWC 15 relative to the ablation probe 19. Alternative similar arrangements may be set up for a biopsy or other procedures. The handle 20 may include an engagement feature 27 for engaging the mating feature of the proximal end 16 of the EWC 15. The engagement feature 27 may be, for example, a clip that is received within an opening defined in the proximal end 16 of the EWC 15.

The ablation catheter assembly 100 includes an ablation probe 19 that extends through the EWC 15. The ablation probe 19 may include a microwave antenna (not shown) electrically connected to cable 18 and sized be received within an outer sheath of the ablation probe 19. The ablation probe 19, and more particularly the microwave antenna, is actively cooled. Examples of microwave antenna construction may be found in commonly assigned U.S. Patent Pub. Nos. 2014/0276033 entitled "Microwave Energy-Device and System," and 2014/0046174 entitled "Microwave Ablation Catheter and Method of Utilizing Same," the entire contents of each is incorporated herein by reference.

The rail system 300 includes rail 312, lower support 520, and device support 530. The lower support 520 includes a support body 522 (FIG. 2A) that mounts to bronchoscope 11 to support the rail 312. The rail 312 has a lower end 314 and an upper end 318, and defines a longitudinal axis therebetween. The device support 530 includes a support collar 532 slidably disposed over the rail 312, instrument fingers 534 extending therefrom, and a locking mechanism 540 disposed therein. The support body 522 of the lower support 520 is coupled to a lower or distal end 314 of the rail 312 and defines a rail opening 524 (FIG. 2A) that receives the lower end of the rail 312 therein.

Figure 2A:
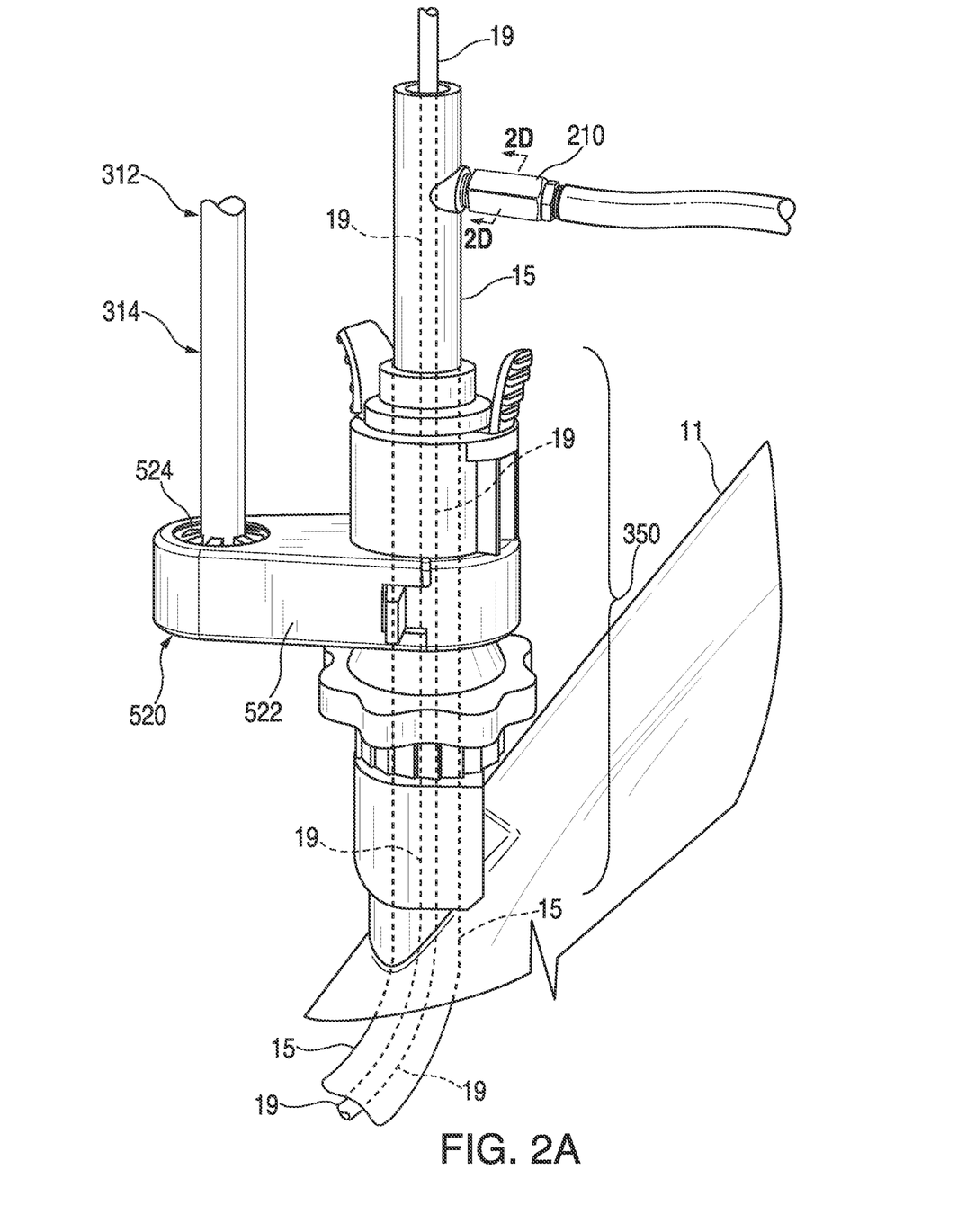
FIG. 2A is an enlarged view of the indicated area of detail of FIG. 1, illustrating a one-way valve connected to an extended working channel (EWC), in accordance with aspects of the present disclosure.
Figures 2B, 2D, 2E:
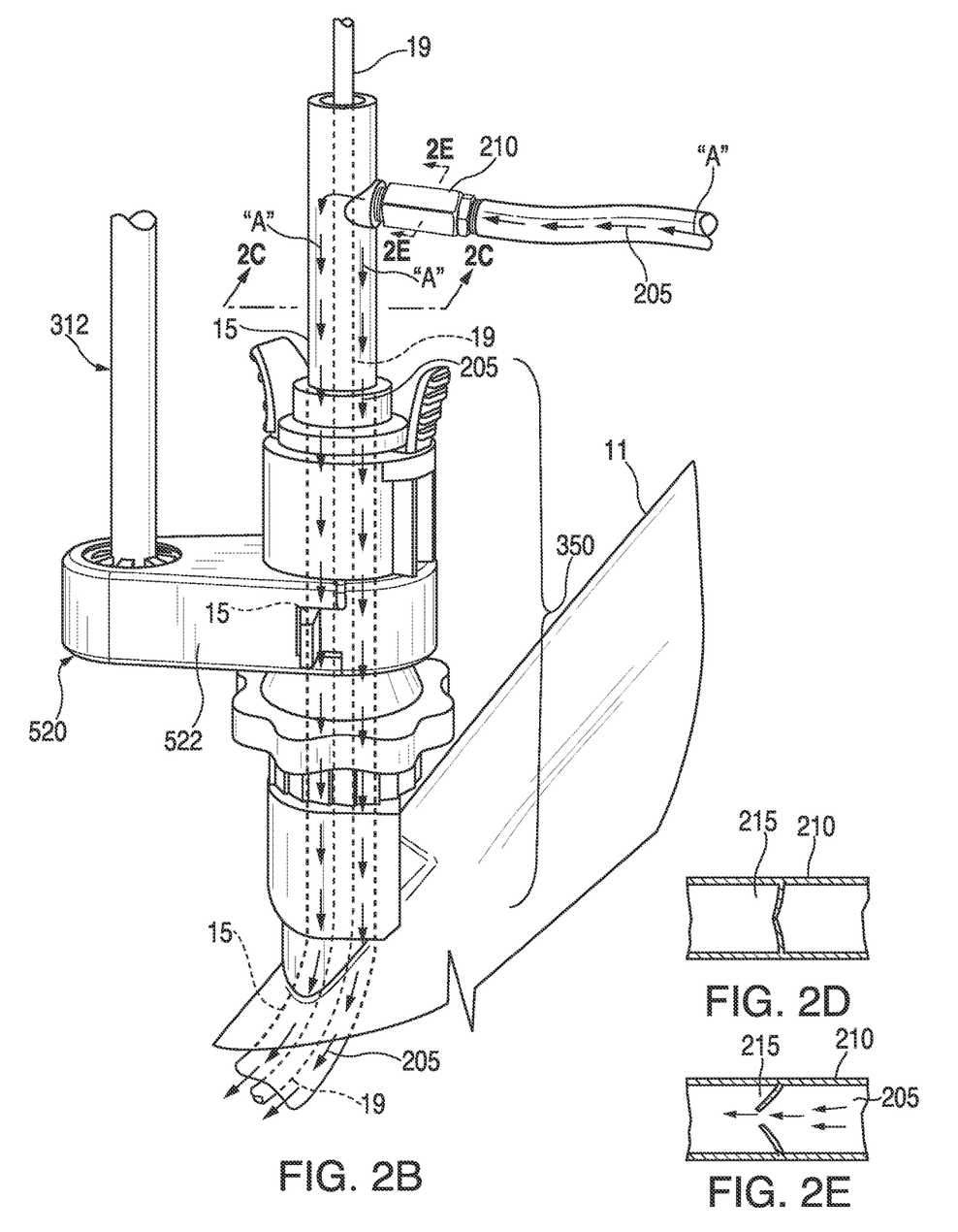
FIG. 2B depicts fluid flow through the one-way valve and the EWC, and into a bronchoscope, in accordance with aspects of the present disclosure.
FIGS. 2D and 2E are cross-sectional views taken along section lines 2D-2D and 2E-2E of FIGS. 2A and 2B, respectively, of the one-way valve depicting a duckbill seal therein, the one-way valve shown in biased and unbiased states, in accordance with aspects of the present disclosure.

FIG. 2A is an enlarged view of the indicated area of detail of FIG. 1, illustrating the one-way valve 210 attached to the EWC 15, in accordance with aspects of the present disclosure. The valve 210 is connected to the EWC 15. In FIG. 2A, no fluid flows through the one-way valve 210. Further, the EWC 15 extends through the upper bronchoscope member 350 and into the bronchoscope 11. Also, the ablation probe 19 extends through an entire length of the EWC 15 and into the bronchoscope 11. The ablation probe 19 is configured to be received within the EWC 15. The one-way valve 210 is connected perpendicular to the EWC 15. The one-way valve 210 may include a duckbill seal 215 therein, as shown in FIGS. 2D and 2E. In FIG. 2D, the duckbill seal 215 is shown in an unbiased state (i.e., no fluid passes therethrough), whereas in FIG. 2E, the duckbill seal 215 is shown in a biased state (i.e., fluid 205 passes therethrough). Of course, one skilled in the art may contemplate any other type of seal used in the one-way valve.

Figure 2C:
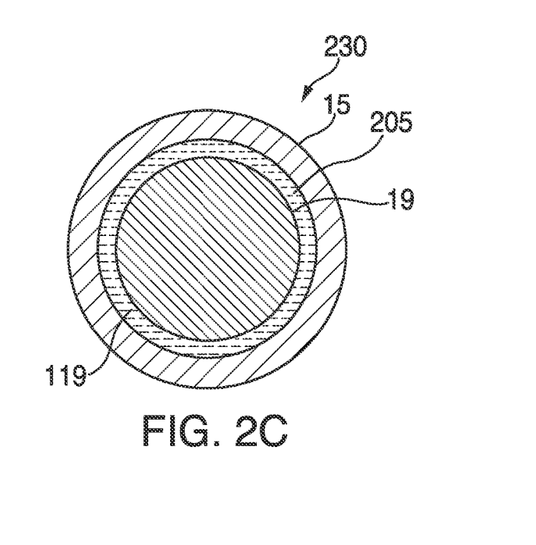
FIG. 2C is a cross-sectional view taken along the section line 2C-2C of FIG. 2B.

FIG. 2B depicts fluid flow through the one-way valve 210 and the EWC 15, in accordance with aspects of the present disclosure. In FIG. 2B, fluid 205 flows through the one-way valve 210 and into the EWC 15. The fluid 205 then flows into the bronchoscope 11 connected to the EWC 15 via the upper bronchoscope member 350. The fluid 205 flows while the ablation probe 19 is positioned within the EWC 15. As a result, the fluid 205 flows in a space 119 defined between the EWC 15 and the ablation probe 19, as shown in FIG. 2C. Space 119 is an annular area defined therebetween. Thus, a clinician may apply a fluid 205 to a surgical site and simultaneously manipulate an instrument (e.g., ablation probe 19) at the surgical site by use of the EWC 15. In this way, the EWC 15 (or primary channel) achieves the dual purpose of allowing a clinician to simultaneously use/manipulate a surgical instrument and apply one or more fluids through EWC 15. Therefore, surgical instrument deployment does not interfere with therapy delivery, as both may be accommodated in tandem within the EWC 15.

FIG. 2C is a cross-sectional view 230 taken along the section line 2C-2C of FIG. 2B. The cross-sectional view 230 illustrates the EWC 15 and the ablation probe 19 positioned within the EWC 15. Space 119 is annularly defined between the EWC 15 and the ablation probe 19. Fluid 205 flowing from the one-way valve 210 is received within the space 119. The fluid 205 travels along the length of the upper bronchoscope member 350 and into the bronchoscope 11, via the EWC 15 (FIG. 2B). The fluid 205 does not directly contact the bronchoscope 11, but stays in the EWC 15 until it exits the EWC 15. The flow of fluid 205 is shown by arrows "A." Fluid 205 flows circumferentially around the ablation probe 19 within the annular space 119.

The fluid 205 may be at least one of the following: a pharmaceutical agent, a contrast agent, a sensitizing agent, a coagulation agent, a therapeutic agent, a diagnostic agent, a hemostasis agent, and an antibiotic, combinations of these and others as would be contemplated by those of ordinary skill in the art for diagnostic and treatment purposes.

Figure 3A:
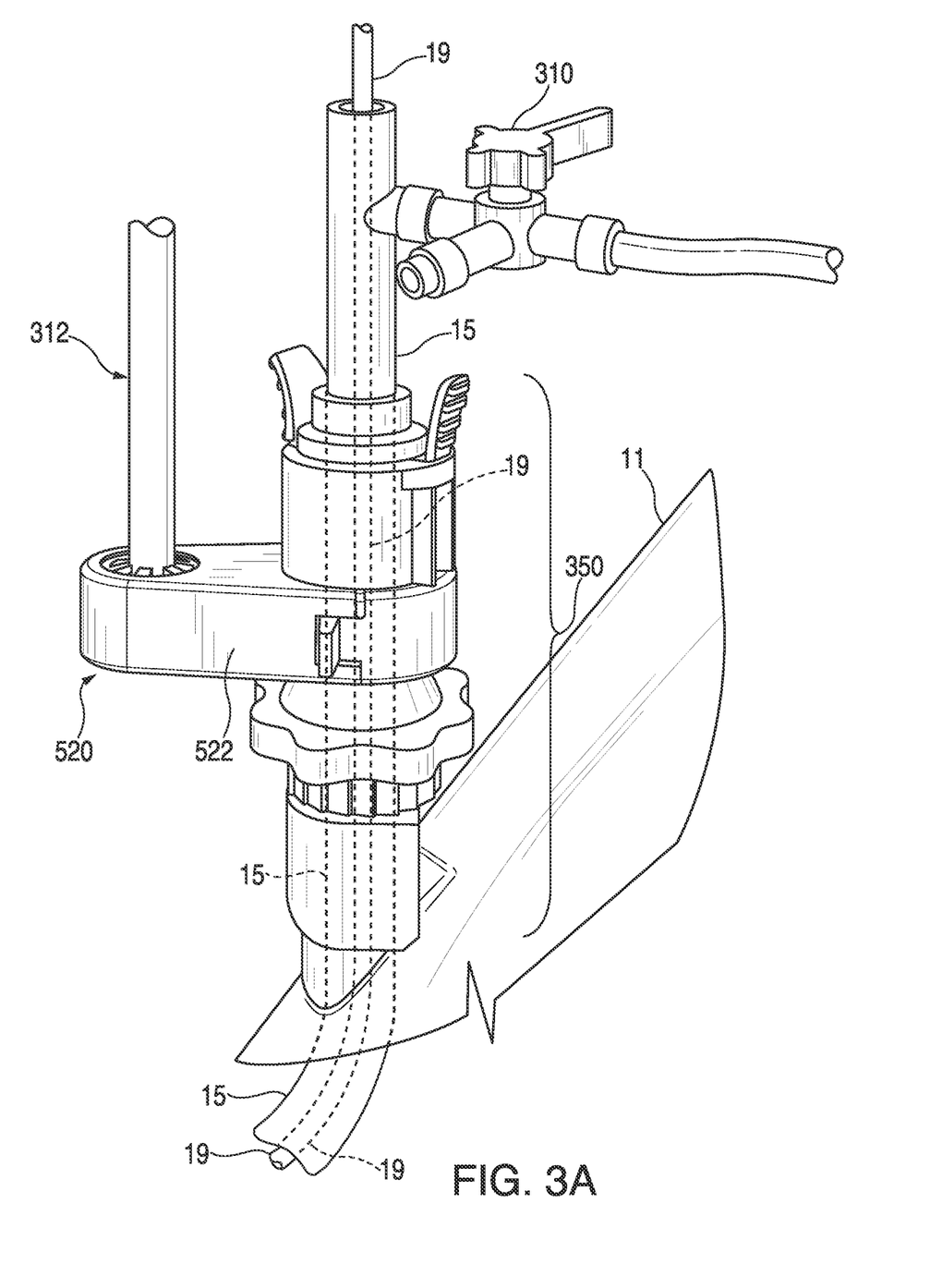
FIG. 3A is an enlarged view illustrating a three-way top cock valve attached to the EWC of the system, in accordance with aspects of the present disclosure.

FIG. 3A is an enlarged view illustrating a three-way top cock valve 310, in accordance with aspects of the present disclosure. The valve 310 is connected to the extended working channel EWC 15. The valve 310 is a three-way stop cock valve. The three-way stop cock valve 310 may provide the user with the ability to suction through one of the pathways. In FIG. 3A, no fluid flows through the three-way stop cock valve 310. Further, as in FIG. 2A, the EWC 15 extends through the upper bronchoscope member 350 and into the bronchoscope 11. Also, the ablation probe 19 extends through an entire length of the EWC 15 and into the bronchoscope 11.

Figure 3B:
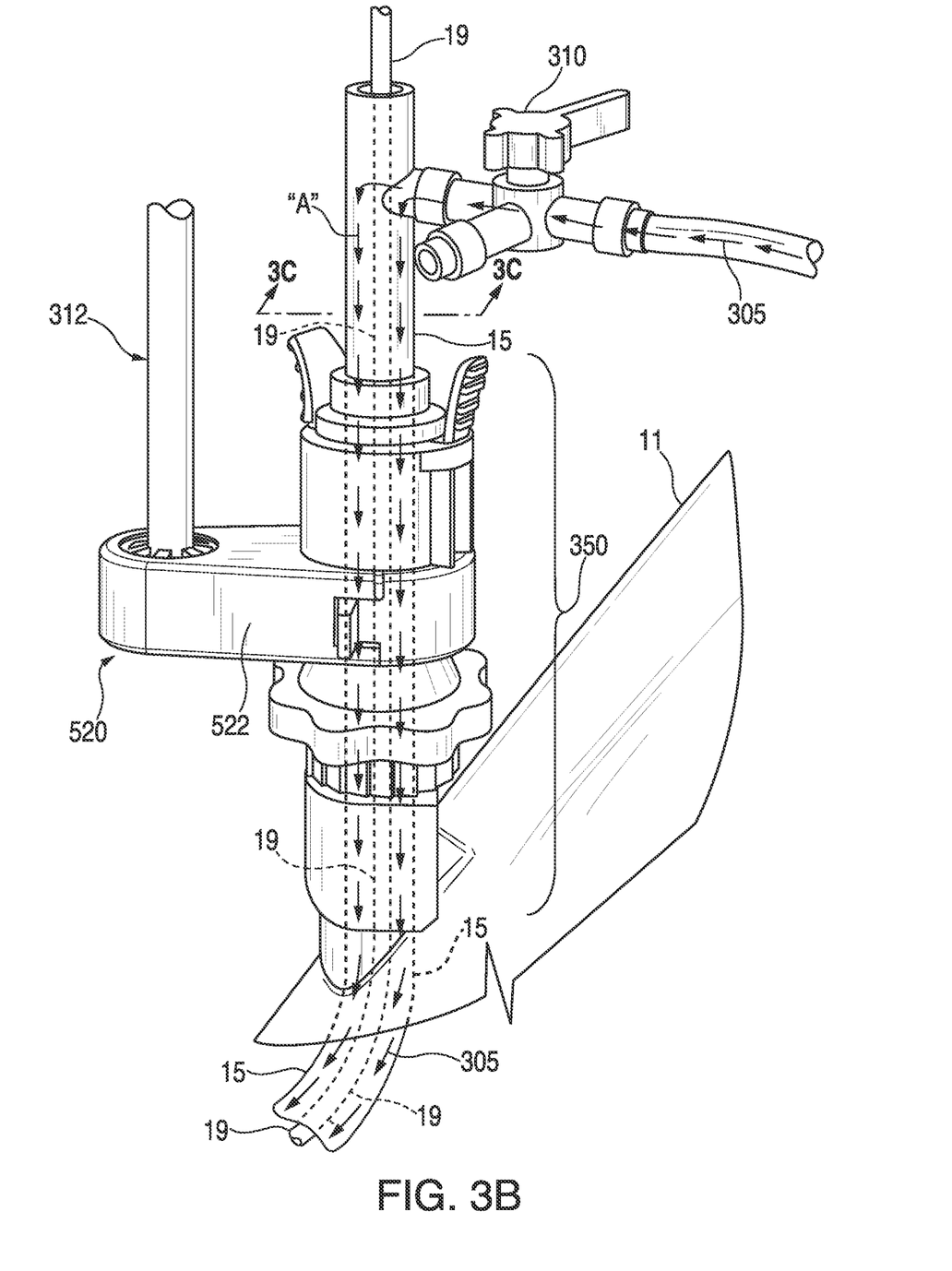
FIG. 3B depicts fluid flow through the three-way stop cock valve and the EWC, in accordance with aspects of the present disclosure.

FIG. 3B depicts fluid flow through the three-way stop cock valve 310 and the extended working channel (EWC) 15, in accordance with aspects of the present disclosure. In FIG. 3B, fluid 305 flows through the three-way stop cock valve 310 and into the EWC 15. The fluid 305 then flows into the bronchoscope 11 connected to the EWC 15 via the upper bronchoscope member 350. The fluid 305 flows while the ablation probe 19 is positioned within the EWC 15. As a result, the fluid 305 flows in a space 219 defined between the EWC 15 and the ablation probe 19, as shown in FIG. 2C. Space 219 is an annular area defined therebetween. Thus, a clinician may apply a fluid 305 to a surgical site and simultaneously manipulate an instrument (e.g., ablation probe 19) at the surgical site by use of the EWC 15. In this way, the EWC 15 (or primary channel) achieves the dual purpose of allowing a clinician to simultaneously use/manipulate a surgical instrument and apply one or more fluids through EWC 15. Therefore, surgical instrument deployment does not interfere with therapy delivery, as both may be accommodated in tandem within the EWC 15.

Figure 4A:
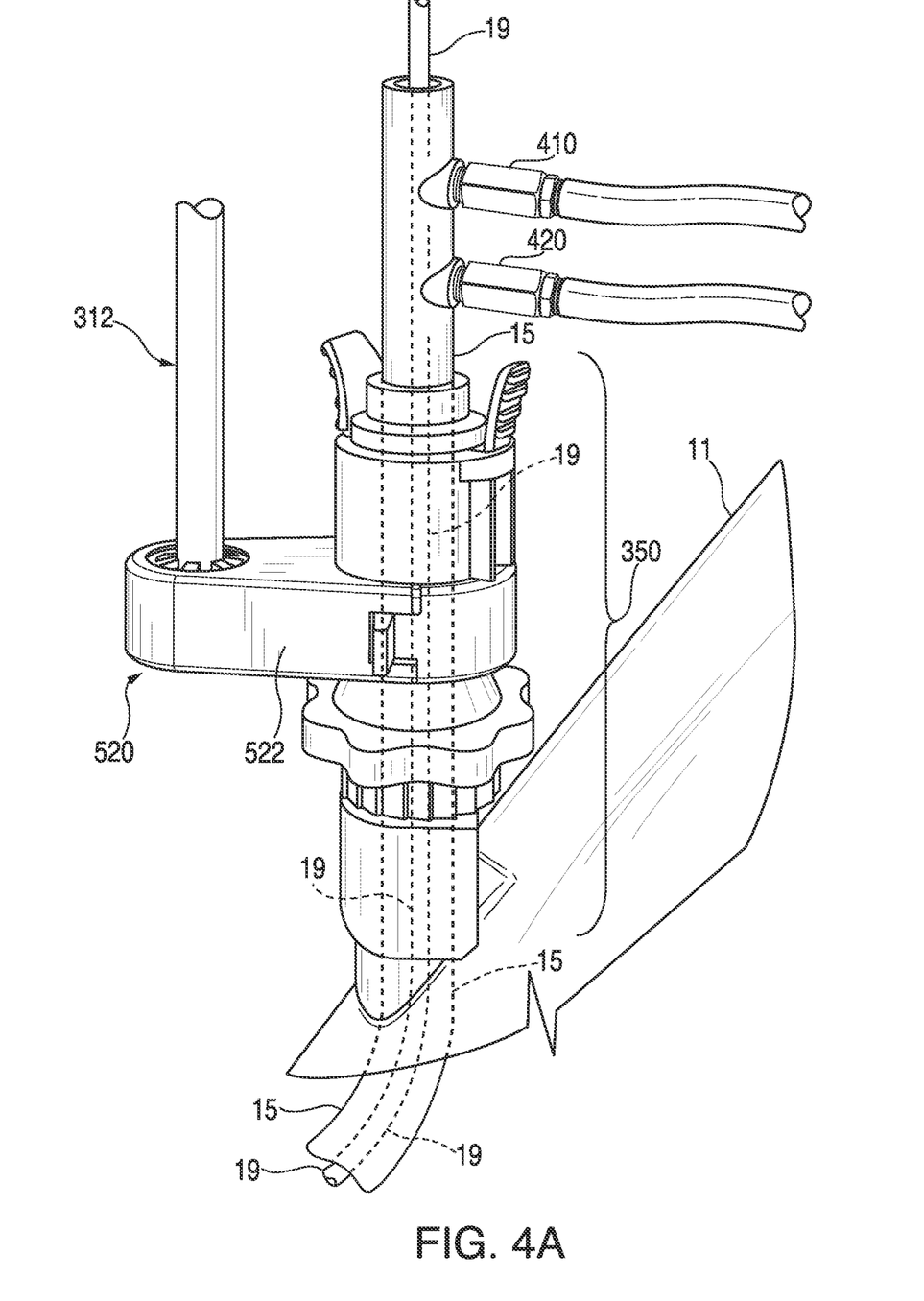
FIG. 4A is an enlarged view illustrating two one-way valves attached to the EWC of the system, in accordance with aspects of the present disclosure.

FIG. 4A is an enlarged view illustrating two one-way valves 410, 420, in accordance with aspects of the present disclosure. Valves 410, 420 are connected to the extended working channel EWC 15. The valves 410, 420 are one-way valves. Valves 410, 420 may be parallel to each other. Valves 410, 420 may be perpendicular to the EWC 15. In FIG. 4A, no fluid flows through the one-way valves 410, 420. Further, the EWC 15 extends through the upper bronchoscope member 350 and into the bronchoscope 11. Also, the ablation probe 19 extends through an entire length of the EWC 15 and into the bronchoscope 11. The ablation probe 19 is configured to be received within the EWC 15.

Figure 4B:
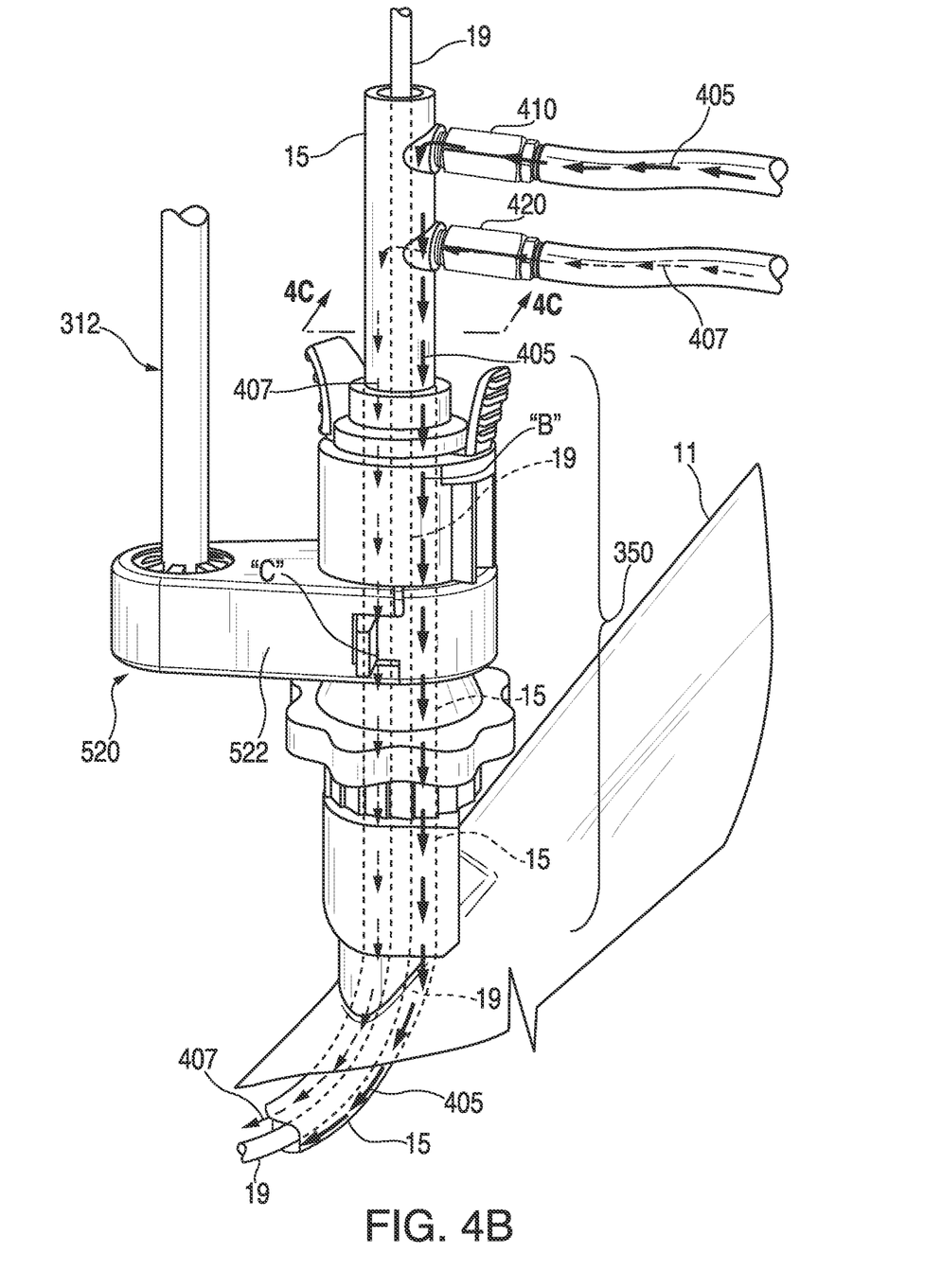
FIG. 4B depicts fluid flow through each of the two one-way valves and the EWC, in accordance with aspects of the present disclosure.
Figure 4C:
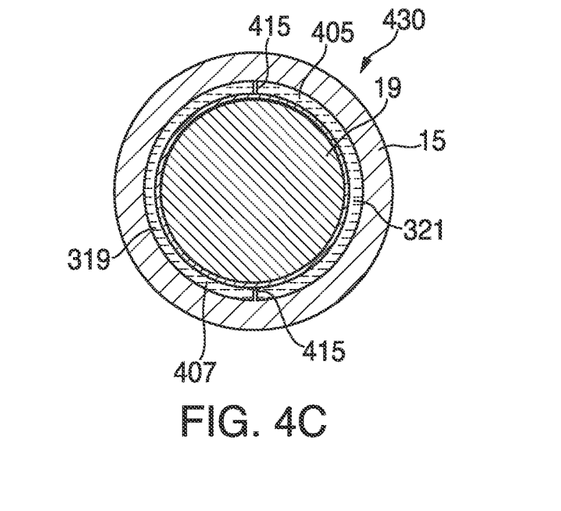
FIG. 4C is a cross-sectional view taken along the section line 4C-4C of FIG. 4B.

FIG. 4B depicts fluid flow through each of the two one-way valves 410, 420 and the extended working channel (EWC) 15, in accordance with aspects of the present disclosure. In FIG. 4B, fluids 405, 407 flow through the one-way valves 410, 420, respectively, and into the EWC 15. Fluid 405 is different than fluid 407. The fluids 405, 407 then flow into the bronchoscope 11 connected to the EWC 15 via the upper bronchoscope member 350. The fluids 405, 407 flow while the ablation probe 19 is positioned within the EWC 15. As a result, the fluids 405, 407 flow in spaces 319, 321, respectively, which are defined between the EWC 15 and the ablation probe 19, as shown in FIG. 4C. Spaces 319, 321 are semi-annular areas defined therebetween. Space 319 may be substantially equal to space 321. Spaces 319, 321 may be substantially hemi-spherically formed spaces divided by walls 415. Dividing walls 415 prevent inadvertent mixing of fluids 405, 407. (FIG. 4C) The dividing walls 415 may be formed on interior portions or walls of the EWC 15.

Thus, a clinician may apply two fluids 405, 407 to a surgical site and simultaneously manipulate an instrument (e.g., ablation probe 19) at the surgical site by use of the EWC 15. In this way, the EWC 15 (or primary channel) achieves the dual purpose of allowing a clinician to simultaneously use/manipulate a surgical instrument and apply one or more fluids through EWC 15. Therefore, surgical instrument deployment does not interfere with therapy delivery, as both may be accommodated in tandem within the EWC 15.

FIG. 4C is a cross-sectional view 430 taken along the section line 4C-4C of FIG. 4B. Spaces 319, 321 are defined between the EWC 15 and the ablation probe 19. Spaces 319, 321 are divided by dividing walls 415. Fluid 405 flowing from the one-way valve 410 is received within space 319 and fluid 407 flowing from the one-way valve 420 is received within space 321. The fluids 405, 407 travel along the length of the upper bronchoscope member 350 and into the bronchoscope 11, via the EWC 15. (FIG. 4B) The fluids 405, 407 do not directly contact the bronchoscope 11, but stay in the EWC 15 until they exit the EWC 15. The flow of fluid 405 is shown by arrows "B" and the flow of fluid 407 is shown by arrows "C."

The fluids 405, 407 may be applied concurrently to the surgical site. Alternatively, the fluids 405, 407 may be successively or independently applied to the surgical site. In this way, the clinician may decide to first apply fluid 405 (e.g., diagnostic agent) and subsequently during the surgical procedure apply fluid 407 (e.g., a therapeutic agent). Thus, the clinician has the ability to control the valves 410, 420 during the surgical procedure.

Figure 5:
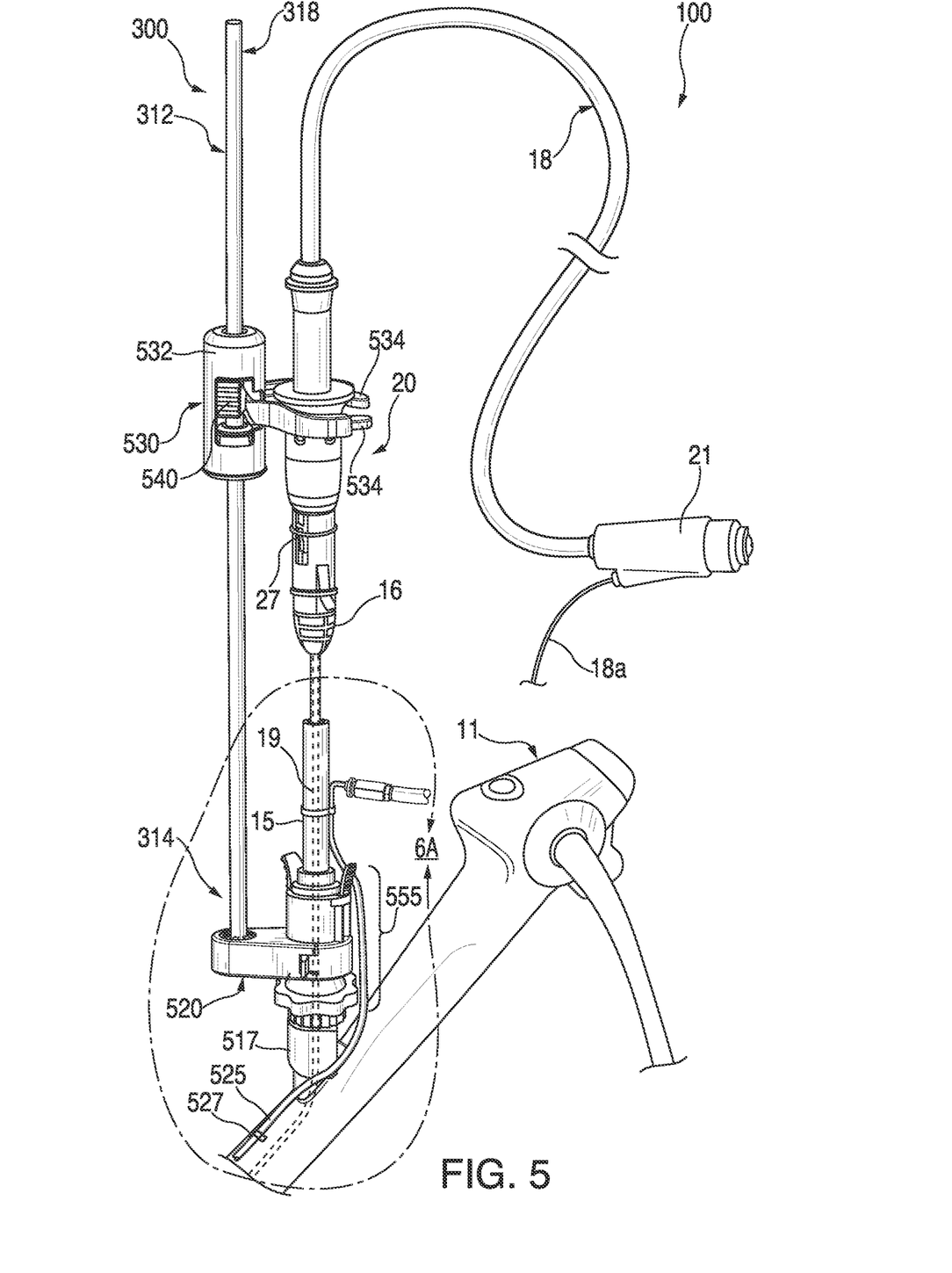
FIG. 5 illustrates a system having a side port attached to an outer surface of the EWC, in accordance with aspects of the present disclosure.

FIG. 5 illustrates a navigation system 500 depicting a side port 525 attached to an outer surface of the EWC 15, in accordance with aspects of the present disclosure. The system 500 includes a bronchoscope 11, an extended working channel (EWC) handle 15, an ablation catheter assembly 100, including a cable 18, a probe 19, a handle 20, and a connector 21 for connection to an energy source such as a microwave generator (not shown). For sake of clarity, similar elements to FIG. 1 will not be described with reference to FIG. 5.

The navigation system 500 includes a valve connected to sidecar arrangement or side port 525 for supplying a fluid 505 (FIG. 6A) to a target site. The valve may be a one-way valve 510 (FIG. 6A) or a three-way stop cock valve 520 (FIG. 6B). Further, the EWC 15 extends through the upper bronchoscope member 555 and into the bronchoscope 11. Also, the ablation probe 19 extends through an entire length of the EWC 15 and into the bronchoscope 11. The ablation probe 19 is configured to be received within the EWC 15.

Side port 525 extends along an outer surface of the EWC 15 and the upper bronchoscope member 555. Side port 525 is connected or fixedly secured to the EWC 15 by attachment mechanisms 527. Attachment mechanisms 527 may be, for example, clips. The ablation probe 19 extends within the bronchoscope 11, whereas the side port 525 extends on an outer surface of the bronchoscope 11. Both the ablation probe 19 and the side port 525 may terminate at a target surgical site.

Rather than seek to force fluid through the EWC 15, side port 525 is slidingly attached on the outside of the bronchoscope 11, and fixedly attached on the outside of the EWC 15 during set-up. Once the bronchoscope 11 is wedged in the airways of a patient (not shown), the EWC 15 begins its navigation and takes the side port 525 which is fixedly attached to the EWC 15, but only slidingly attached to the bronchoscope 11. This allows the side port 525 to be drawn along with the EWC 15 (in a sidecar arrangement) as the EWC 15 is navigated to a target area. In one arrangement the side port 525 is used to supply fluid, hydrophilic or hydrophobic materials, salts, and/or a vacuum as necessary for a given procedure.

Figure 6A:
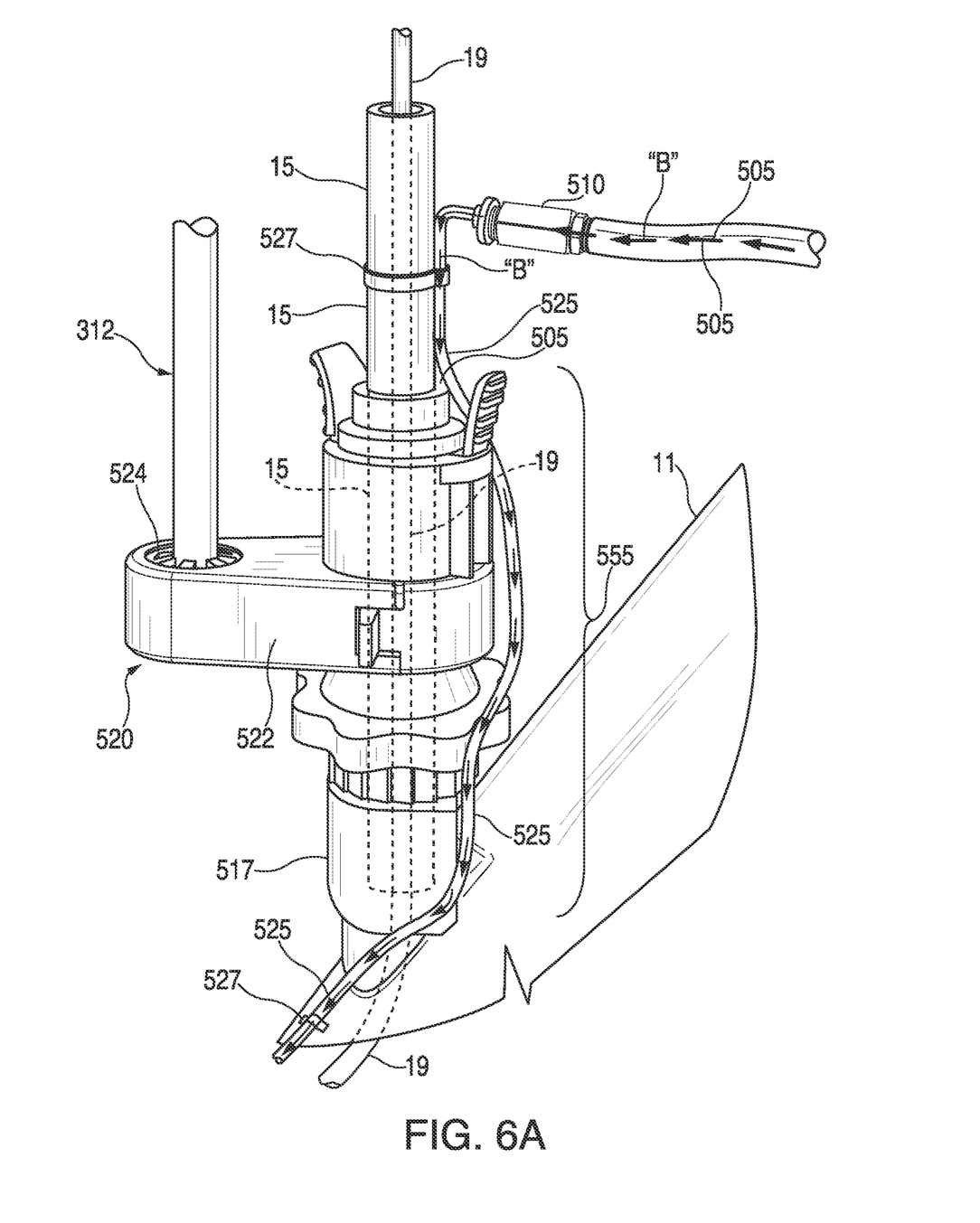
FIG. 6A is an enlarged view of the indicated area of detail of FIG. 5, illustrating a one-way valve connected to the side port, in accordance with aspects of the present disclosure.
Figure 6B:
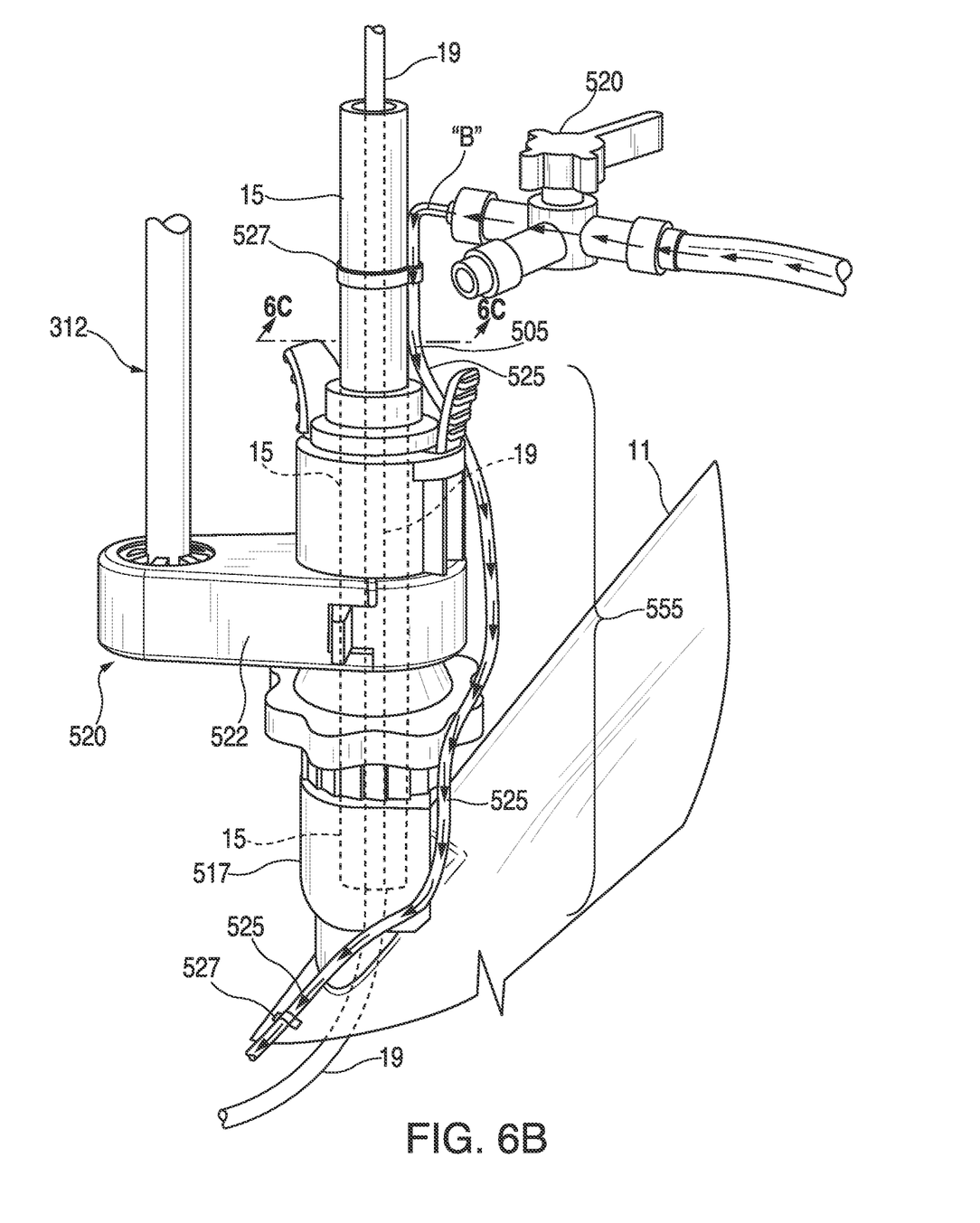
FIG. 6B depicts a three-way stop cock valve connected to the side port, in accordance with aspects of the present disclosure.

FIG. 6A is an enlarged view of the indicated area of detail of FIG. 5, illustrating a one-way valve 510 connected to the side port 525, in accordance with aspects of the present disclosure. The valve 510 is connected to the extended working channel EWC 15. The valve 510 is a one-way valve. In FIG. 6A, fluid 505 flows through the one-way valve 510 and into the side port 525. The fluid flow is indicated by arrows "B." The fluid 505 then flows into the bronchoscope 11 connected to the EWC 15 on the outside surface of the upper bronchoscope member 555.

Thus, a clinician may apply a fluid 505 to a surgical site by side port 525 and simultaneously manipulate an instrument (e.g., ablation probe 19) at the surgical site by use of the EWC 15. In this way, the EWC 15 (or primary channel) remains free of fluid and surgical instrument deployment via the primary channel does not interfere with therapy delivery, as both may be accommodated in tandem with the EWC 15 and the side port 525.

FIG. 6B depicts a three-way stop cock valve 520 connected to the side port 525, in accordance with aspects of the present disclosure. The valve 520 is connected to the extended working channel EWC 15. The valve 520 is a three-way stop cock valve. In FIG. 6B, fluid 505 flows through the three-way stop cock valve 520 and into the side port 525. The fluid 505 then flows into the bronchoscope 11 connected to the EWC 15 and onto an outer surface of the upper bronchoscope member 555. The fluid 505 in the side port 525 flows without interfering with the ablation probe 19, which is positioned within the EWC 15. Thus, fluid flow 505 does not affect the operation of the ablation probe 19 by a user.

Therefore, a clinician may apply a fluid 505 to a surgical site by side port 525 and simultaneously manipulate an instrument (e.g., ablation probe 19) at the surgical site by use of the EWC 15. In this way, the EWC 15 (or primary channel) remains free of fluid and surgical instrument deployment via the primary channel does not interfere with therapy delivery, as both may be accommodated in tandem with the EWC 15 and the side port 525.

Figure 6C:
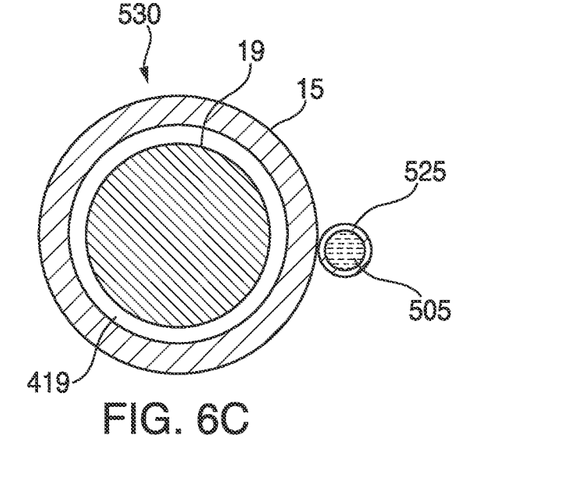
FIG. 6C is a cross-sectional view taken along the section line 6C-6C of FIG. 6B.

FIG. 6C is a cross-sectional view 530 taken along the section line 6C-6C of FIG. 6B. The cross-sectional view 530 illustrates the EWC 15 and the ablation probe 19 positioned within the EWC 15. Space 419 is defined between the EWC 15 and the ablation probe 19. Space 419 is an annular space. Space 419 remains free of fluid, since the fluid 505 flows to the target surgical site via the side port 525. The cross-sectional view 530 further illustrates the side port 525 adjacent the EWC 15. There is no fluid communication between the EWC 15 and the side port 525.

Fluid 505 flowing from the one-way valve 510 is received within the side port 525. The fluid 505 travels along the length of an outer surface of the upper bronchoscope member 555 and into the bronchoscope 11, via the EWC 15 (FIG. 6A). The fluid 505 does not directly contact the bronchoscope 11, but stays in the EWC 15 until it exits the EWC 15. The flow of fluid 505 is shown by arrows "B." (FIG. 6A). Thus, the fluid 505 flows through the side port 525 (instead of the EWC 15, as shown in FIGS. 2A-4C) such that the primary channel remains free of fluid.

Figure 7:
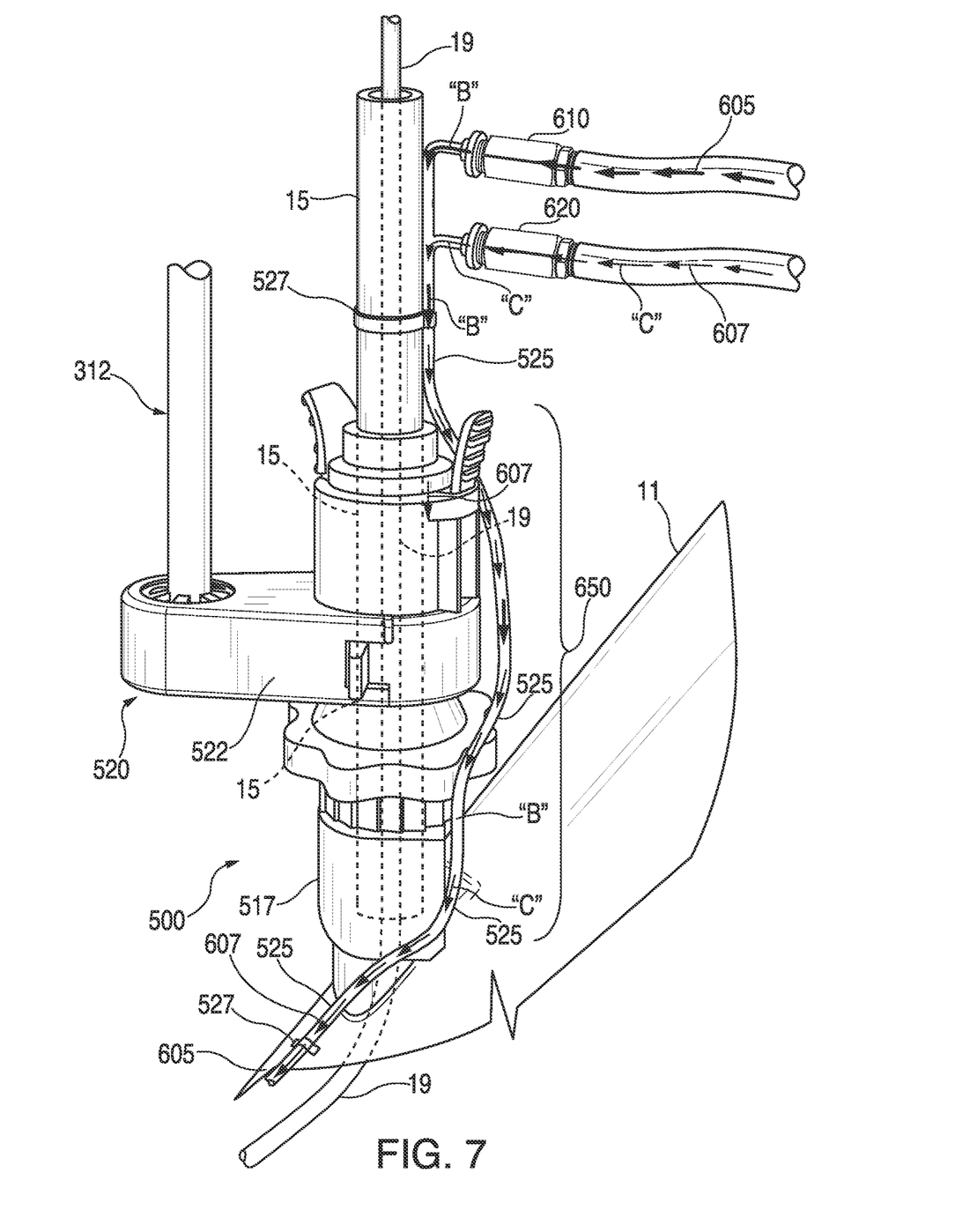
FIG. 7 depicts two one-way valves connected to the side port, in accordance with aspects of the present disclosure.

FIG. 7 depicts two one-way valves 610, 620 connected to the side port 525, in accordance with aspects of the present disclosure. Valves 610, 620 are connected to the extended working channel EWC 15. The valves 610, 620 are one-way valves. Of course, one skilled in the art may contemplate using two three-way stop cock valves. Alternatively, one skilled in the art may contemplate using a single one-way valve and a single three-way stop cock valve in tandem.

In FIG. 7, fluids 605, 607 flow through the one-way valves 610, 620, respectively, and into the EWC 15. Fluid 605 is different than fluid 607. The fluids 605, 607 then flow to the surgical site via the side port 525 attached to the upper bronchoscope member 650 and the outer surface of the bronchoscope 11. Fluid 605 is indicated by arrows "B" and fluid 607 is indicated by arrows "C." The fluids 605, 607 flow without interfering with the operation of the ablation probe 19, which is positioned within the EWC 15. As a result, the fluids 605, 607 flow in the navigation system 500 via the side port 525. The fluids 605, 607 may be applied concurrently to the surgical site. Alternatively, the fluids 605, 607 may be successively or independently applied to the surgical site. In this way, the clinician may decide to first apply fluid 605 (e.g., diagnostic agent) and subsequently during the surgical procedure apply fluid 607 (e.g., a therapeutic agent). Thus, the clinician has the ability to control the valves 610, 620 during the surgical procedure.

As a result, a clinician may apply two fluids 605, 607 to a surgical site and simultaneously manipulate an instrument (e.g., ablation probe 19) at the surgical site by use of the EWC 15 and the side port 525. In this way, the EWC 15 (or primary channel) remains free of fluid and surgical instrument deployment via the primary channel does not interfere with therapy delivery, as both may be accommodated in tandem with the EWC 15 and the side port 525.

Detailed embodiments of devices, systems incorporating such devices, and methods using the same as described herein. However, these detailed embodiments are merely examples of the disclosure, which may be embodied in various forms. Therefore, specific structural and functional details disclosed herein are not to be interpreted as limiting, but merely as a basis for the claims and as a representative basis for allowing one skilled in the art to variously employ the present disclosure in appropriately detailed structure. While the preceding embodiments are described in terms of bronchoscopy of a patient's airways, those skilled in the art will realize that the same or similar devices, systems, and methods may be used in other lumen networks, such as, for example, the vascular, lymphatic, and/or gastrointestinal networks as well.

While the use of the handle 20 and the rail system 300 are detailed herein for use in the airway of a patient, it is contemplated that the handle 20 and/or the rail system 300 may be used in a variety of surgical procedures utilizing elongated surgical instruments with extended working channels. For example, the handle 20 and or rail system 300 may be used to stabilize a guide wire or catheter during various endovascular procedures such as cardiac interventions, general vascular interventional procedures, cerebral interventions, etc. These procedures may include, but are not limited to, balloon dilations, stent placements, percutaneous valve replacement, percutaneous valve repair, pacing lead placement, cardiac ablation procedures, and electrical mapping procedures.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope and spirit of the claims appended hereto.

What is claimed is:

1. A surgical system, comprising:
a bronchoscope having a working channel;
a rail system configured to be coupled to the bronchoscope;
a catheter including a mating feature and configured to be positioned through the working channel of the bronchoscope; and
an ablation catheter including an engagement feature, the engagement feature configured to couple with the mating feature of the catheter, wherein the ablation catheter is coupled to the rail system, and wherein the catheter is configured to position a distal portion of the ablation catheter at a surgical side within the patient.

2. The surgical system according to claim 1, wherein the rail system includes a lower support at a distal end of the rail system, the lower support releasably coupling the rail system and the bronchoscope and supporting the rail system relative to the bronchoscope.

3. The surgical system according to claim 1, wherein the ablation catheter is configured to be inserted through a lumen of the catheter, the ablation catheter having a handle, wherein the catheter is movable relative to the ablation catheter.

4. The surgical system according to claim 3, wherein the handle of the ablation catheter is configured to be releasably engaged by a device support slidingly coupled to the rail system to support the ablation catheter relative to the bronchoscope.

5. The surgical system according to claim 1, further comprising a valve coupled to the catheter and disposed in fluid communication with a lumen of the catheter.

6. The surgical system according to claim 5, wherein the valve is located outside of an outer surface of the catheter.

7. The surgical system according to claim 5, wherein the valve is configured to permit a flow of a fluid through the valve and through the lumen of the catheter such that the fluid is delivered via the catheter to the surgical site.

8. The surgical system according to claim 7, wherein the fluid includes at least one of a pharmaceutical agent, a contrast agent, a sensitizing agent, a coagulation agent, a therapeutic agent, a diagnostic agent, a hemostasis agent, or an antibiotic.

* * * * *